(12) United States Patent
Tagawa et al.

(10) Patent No.: US 9,968,311 B2
(45) Date of Patent: May 15, 2018

(54) RADIATION IMAGING SYSTEM AND RADIOGRAPHY SYSTEM

(71) Applicant: CANON KABUSHIKI KAISHA, Tokyo (JP)

(72) Inventors: Motoki Tagawa, Chigasaki (JP); Masataka Suzuki, Kawasaki (JP); Ryo Suzaki, Tokyo (JP); Shichihei Sakuragi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 240 days.

(21) Appl. No.: 15/082,343

(22) Filed: Mar. 28, 2016

(65) Prior Publication Data
US 2016/0287195 A1    Oct. 6, 2016

(30) Foreign Application Priority Data

Mar. 31, 2015   (JP) .................. 2015-072873

(51) Int. Cl.
*A61B 6/04*    (2006.01)
*A61B 6/08*    (2006.01)
*A61B 6/00*    (2006.01)

(52) U.S. Cl.
CPC .............. *A61B 6/08* (2013.01); *A61B 6/4266* (2013.01); *A61B 6/4452* (2013.01); *A61B 6/465* (2013.01); *A61B 6/5241* (2013.01); *A61B 6/587* (2013.01); *A61B 6/4291* (2013.01)

(58) Field of Classification Search
CPC ..... A61B 6/4266; A61B 6/463; G01T 1/2006; G01T 1/1603; G01T 1/20
See application file for complete search history.

(56) References Cited

U.S. PATENT DOCUMENTS

2013/0114790 A1*   5/2013   Fabrizio ................... A61B 6/02
378/62

FOREIGN PATENT DOCUMENTS

JP    11-244270 A    9/1999
JP    2012-040140 A    3/2012

* cited by examiner

*Primary Examiner* — Don Wong
(74) *Attorney, Agent, or Firm* — Canon USA Inc., IP Division (57) ABSTRACT

A radiation imaging system includes a holding unit configured to hold a plurality of radiation imaging apparatuses configured to convert radiation emitted onto the plurality of radiation imaging apparatuses into image signals. The radiation imaging system is configured to obtain a long radiographic image based on the image signals respectively from the plurality of radiation imaging apparatuses. The holding unit is configured to hold the plurality of radiation imaging apparatuses having imaging areas of different sizes, in such a manner that the plurality of radiation imaging apparatuses is partially overlapped with each other spatially, by a predetermined overlapping area as viewed from a radiation incident side.

17 Claims, 8 Drawing Sheets

RADIATION IMAGING SYSTEM AND RADIOGRAPHY SYSTEM

BACKGROUND OF THE INVENTION

Field of the Invention

The present invention relates to a radiation imaging system and a radiography system applied to a medical imaging apparatus, a nondestructive testing apparatus, an analyzing apparatus using radiation, and the like.

Description of the Related Art

In recent years, there has been a demand, in a medical field for example, for performing imaging to obtain an image with a long observed area (hereinafter, referred to as long-length imaging) to obtain an image entirely including the spine or the lower limbs or of the entire body, so that distortion and abnormality of the body of a subject can be checked. The radiation imaging system, capable of performing the long-length imaging by emitting radiation for a single time, leads to smaller amounts of body movement and radiation exposure of the subject, and thus is more preferable than a configuration of performing long-length imaging by emitting the radiation a plurality of times for the observed area divided into a plurality of sections.

Japanese Patent Application Laid-Open No. 2012-040140 discusses a radiation imaging system that can perform long-length imaging by emitting radiation for a single time, with a plurality of radiation imaging apparatuses arranged in a longitudinal direction of the long-length imaging while being partially overlapped with each other spatially, as viewed from a radiation emitting side. Japanese Patent Application Laid-Open No. H11-244270 discusses a supporting member with which radiation imaging apparatuses are arranged while being partially overlapped with each other spatially as viewed from the radiation emitting side.

In the radiation imaging systems discussed in Japanese Patent Application Laid-Open No. 2012-040140 and Japanese Patent Application Laid-Open No. H11-244270, a plurality radiation imaging apparatuses of the same size is used therein. However, in an actual medial field, it may be difficult to prepare a plurality of radiation imaging apparatuses of the same size, and thus a plurality radiation imaging apparatuses of different sizes is used in many cases. A holding unit that holds the radiation imaging apparatuses at their proper positions is not discussed in Japanese Patent Application Laid-Open No. 2012-040140. A specific configuration of the holding unit that holds the radiation imaging apparatuses at their positions is not discussed in Japanese Patent Application Laid-Open No. H11-244270.

SUMMARY OF THE INVENTION

The present invention is directed to a radiation imaging system that can perform long-length imaging with a plurality of radiation imaging apparatuses of different sizes.

A radiation imaging system according to the present invention includes a holding unit configured to hold a plurality of radiation imaging apparatuses configured to convert radiation emitted onto the plurality of radiation imaging apparatuses into image signals. The radiation imaging system is configured to obtain a long radiographic image based on the image signals respectively from the plurality of radiation imaging apparatuses. The holding unit is configured to hold the plurality of radiation imaging apparatuses having imaging areas of different sizes, in such a manner that the plurality of radiation imaging apparatuses is partially overlapped with each other spatially, by a predetermined overlapping area as viewed from a radiation incident side.

Further features of the present invention will become apparent from the following description of exemplary embodiments with reference to the attached drawings.

DESCRIPTION OF THE EMBODIMENTS

Exemplary embodiments of the present invention will be described below in detail with reference to the attached drawings. It is to be noted that detailed sizes and configurations, described in each exemplary embodiment, are not limited to those described in the specification and illustrated in the drawings. Radiation, described in this specification, not only includes X rays, but also includes α rays, β rays, γ rays, particle beams, and cosmic rays.

Figure 1A:
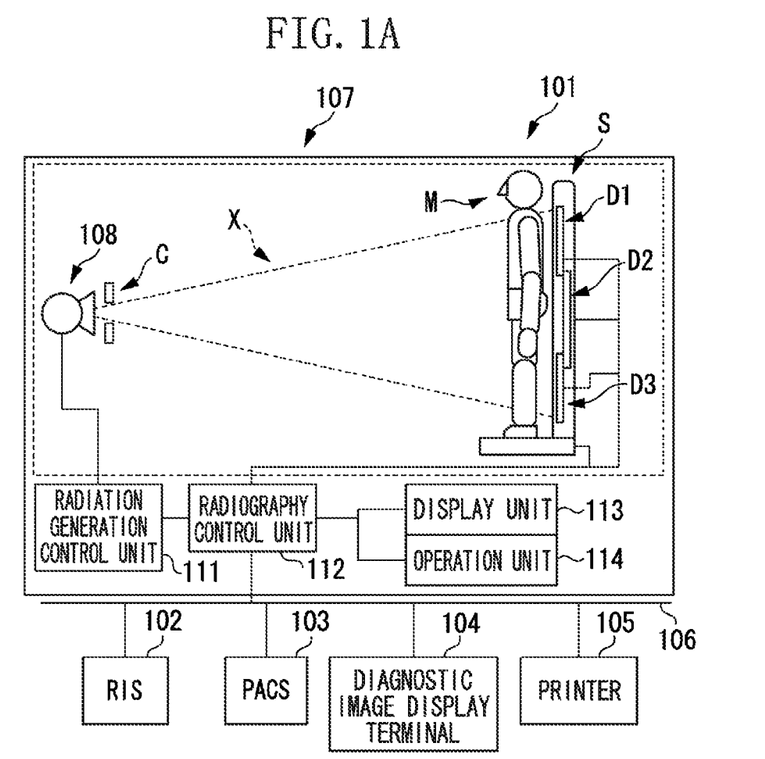
FIGS. 1A and 1B are schematic diagrams illustrating a radiation imaging system according to an exemplary embodiment of the present invention.
Figure 1B:
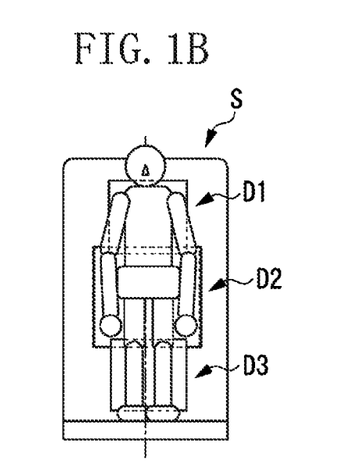

First, a medical diagnosis system is described with reference to FIGS. 1A and 1B. FIGS. 1A and 1B are schematic cross-sectional views illustrating the medical diagnosis system.

A medical diagnosis system 101 includes a radiology information system (RIS) 102, a picture archiving and communication system (PACS) 103, a diagnostic image display terminal 104, a printer 105, and a radiography system 107 that are connected to each other through a communication system 106 such as a wired or wireless network.

The RIS 102 is a system that manages inspection using a radiation device, processes from reservation for medical treatment to inspection results. For example, this system may be an information management system that performs overall management on additional information provided to a radiographic image and an inspection order. The additional information may include inspection information including an inspection identification (ID) or a reception number. An operator can input the inspection order (inspection instruction) through the RIS 102. The radiography system 107 performs imaging based on the inspection order. In the present exemplary embodiment, the input inspection order is stored and managed by the RIS 102. Alternatively, the input inspection order may be stored and managed by a server (not illustrated) connected to the RIS 102 and the radiography system 107. In another exemplary embodiment, the input inspection order may be stored and managed by the radiography system 107.

The PACS 103 stores and manages a digital radiographic image (hereinafter, referred to as a captured image) obtained by the radiography system 107. Thus, the PACS 103 may function as a part of an image management system that manages the captured image. The diagnostic image display terminal 104 can output the captured image, stored in the PACS 103, by displaying the image. The printer 105 can output the captured image, stored in the PACS 103, by printing the image.

The radiography system 107 performs an inspection (imaging) based on an inspection order including a plurality of pieces of inspection information. The inspection information includes information on imaging protocols each defining an imaging condition, a content of image processing executed on the captured image, or the like. More specifically, the imaging protocols each include parameter information or executed imaging information as well as imaging environment information indicating a sensor type, an imaging orientation, and the like used for imaging, image processing, or the like. The inspection information includes information such as the inspection ID and the reception number, for identifying the inspection order or identifying the captured image corresponding to the inspection order.

The radiography system 107 includes a radiation imaging system S, a radiation source 108, a radiation generation control unit 111, a radiography control unit 112, a display unit 113, and an operation unit 114. The radiation imaging system S includes radiation imaging apparatuses D1, D2, and D3. The radiation source 108 functions as a radiation generation unit. More specifically, the radiation source 108 according to the present exemplary embodiment is an X-ray tube that emits radiation (X-rays in this exemplary embodiment) onto an object (subject). The radiation source 108 is provided with a collimator C that delimits an irradiation area irradiated with the radiation. Each of the radiation imaging apparatuses D1, D2, and D3 includes a radiation detection panel, and performs imaging based on the radiation that has passed through the subject. The radiation detection panel includes a pixel array, including a plurality of pixels arranged in a two-dimensional matrix, and converts the radiation emitted thereon into an image signal. A sensor that converts the radiation into an electric signal may be a direct conversion sensor that directly converts radiation into an electrical signal such as an amorphous Selenium (a-Se) sensor, or may be an indirect sensor using a scintillator and a photoelectric conversion element such as a Cesium Iodide (CsI) sensor. The radiation imaging apparatuses D1, D2, and D3 each perform analog-to-digital (A/D) conversion on the electrical signal thus obtained by the conversion, to generate a captured image that is radiographic image data, and transmits the captured image to the radiography control unit 112.

In the system illustrated in FIGS. 1A and 1B, the first and the third radiation imaging apparatuses D1 and D3 are disposed on the radiation source 108 side, that is, on a radiation emitting side more than the second radiation imaging apparatus D2 is. The first and the third radiation imaging apparatuses D1 and D3 are disposed to partially overlap spatially with the second radiation imaging apparatus D2, as viewed from the radiation emitting side. The spatially overlapping state may include an overlapping state involving physical contact and an overlapping state with spaces provided in between and thus involving no physical contact. These overlapping areas enable images to be combined. Thus, the overlapping areas are essential in a case where radiation imaging apparatuses of different sizes are used. With the radiation imaging apparatuses overlapped in the order of a front side, a rear side, and the front side from an upper stage, an enlargement factor can be prevented from being large at upper and lower ends.

As illustrated in FIG. 1B, the radiation imaging apparatuses D1, D2, and D3 have imaging areas of different sizes, each corresponding to an area in which the pixel array is disposed. More specifically, as an example in the present exemplary embodiment, the radiation imaging apparatus D2, disposed at the center, has a large imaging area. The radiation imaging apparatuses D1 and D3, respectively disposed on upper and lower sides, each have an imaging area smaller than that of the radiation imaging apparatus D2. In this example, the radiation imaging apparatuses have different sizes corresponding to the sizes of the imaging areas. With the system that can use the radiation imaging apparatuses of different sizes as described above, a long radiographic image can be obtained by using the radiation imaging apparatuses having different sizes in combination, and thus is advantageous in a case where it is difficult to prepare a plurality of radiation imaging apparatuses of the same size. The present exemplary embodiment is not limited to the example where only the radiation imaging apparatus D2, disposed at the center, has a large imaging area, and the radiation imaging apparatusesD1, D2, and D3 with the sizes described above may be arranged in any desired order. Furthermore, a case where the radiation imaging apparatuses all have a large imaging area, and a case where the radiation imaging apparatuses all have a small imaging area may be selected as desired. In other words, a similar effect can be obtained with a plurality of radiation imaging apparatuses, having imaging areas of different sizes, being able to be combined in any desired way to be used. Generally, a radiation imaging apparatus having a large imaging area has an external size of 46 cm×46 cm and an imaging area of 43 cm×43 cm, whereas a radiation imaging apparatus having a small imaging area has an external size of 46 cm×38 cm and an imaging area of 43 cm×35 cm. The radiation imaging apparatus having a small imaging area in this system has a rectangular imaging area and external shape. Thus, whether this radiation imaging apparatus has a lateral or longitudinal orientation can be selected as desired. More specifically, the radiation imaging apparatus may have the lateral orientation to obtain an imaging area that is long in a lateral direction (width direction), and may have the longitudinal orientation to obtain an imaging area that is long in a longitudinal direction. A configuration of the radiation imaging system S in which the sizes and the orientations of the radiation imaging apparatuses can be selected as desired as described above, is described in detail below.

The radiation generation control unit 111 controls generation of radiation based on the imaging protocols, under control performed by the radiography control unit 112. More specifically, the radiation generation control unit 111 applies voltage to the radiation source 108 and thus causes the radiation source 108 to generate radiation, in accordance with an imaging condition (for example, parameters such as tube current, tube voltage, and an irradiation time) corresponding to the imaging protocols.

The radiography control unit 112 performs overall control on radiography processing based on the imaging protocols. The radiography control unit 112 executes image processing on the image obtained from the radiation imaging system S. The image processing includes combining processing, correction processing, gradation processing, frequency processing, and the like executed on a plurality of images obtained from the radiation imaging apparatuses D1, D2, and D3. The radiography control unit 112 executes the image processing by using image processing parameters corresponding to the imaging protocols. Information on the sizes and the orientations of the radiation imaging apparatuses D1, D2, and D3 is also required for the image processing. In the present exemplary embodiment, the information on the sizes and the orientations of the radiation imaging apparatuses D1, D2, and D3 is transmitted from the radiation imaging system S to the radiography control unit 112. This information may be set in the imaging protocols in advance or may be input by the operator when the imaging is performed. The radiography control unit 112 can transmit the captured image to an external device such as the PACS 103 or the printer 105. The PACS 103 stores the captured image transmitted thereto, together with the inspection information for identifying this captured image. For example, the inspection information may be the inspection ID, the reception number, or the like provided to the inspection order. The inspection order may be stored in the PACS 103 while being associated with the corresponding captured image.

The display unit 113 displays information on a system state or the like to the operator. For example, the display unit 113 may be a display. For example, the display unit 113 may display the inspection order received from the RIS 102 or an inspection order generated by the operator of the radiography system 107. The operation unit 114 acquires an instruction from the operator. For example, the operation unit 114 may be a keyboard, a mouse, various buttons, or the like. For example, the operator may input an instruction to copy an image to the radiography system 107, through the operation unit 114.

Figure 2:
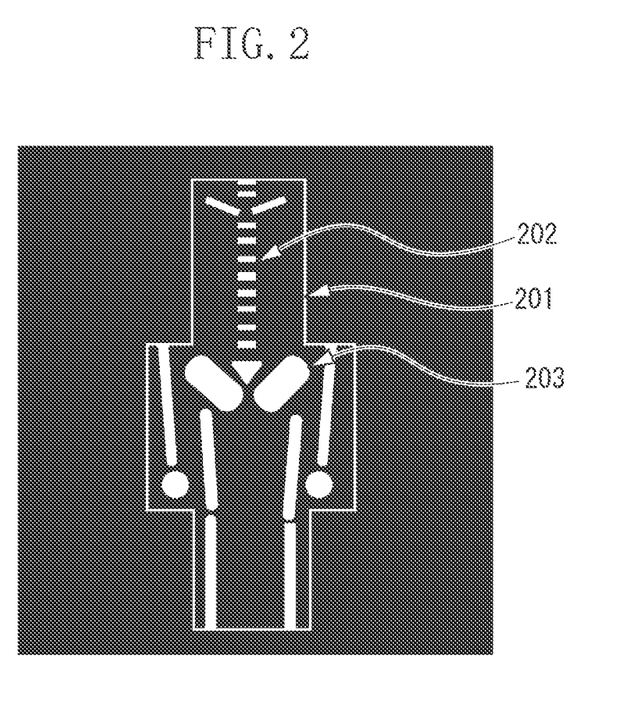
FIG. 2 is a schematic diagram illustrating an obtained long radiographic image.

As illustrated in FIGS. 1A and 1B, the radiation imaging apparatus D2 at the center is larger than the other radiation imaging apparatuses D1 and D3. Therefore, as illustrated in FIG. 2, which illustrates a long radiographic image obtained by the radiation imaging system S illustrated in FIGS. 1A and 1B, in a long radiographic image obtained by the radiation imaging system S, an image in a center portion is larger than images in other portions. In FIG. 2, a spine 202 and a pelvis 203 require different widths of imaging areas. More specifically, the pelvis 203 requires a larger width than the spine 202 does. Thus, a long image (radiographic image) including desired imaging areas can be obtained using the radiation imaging apparatus D2 that images the pelvis 203, having a larger imaging area than that of the radiation imaging apparatus D1 that images the pelvis 203. As illustrated in FIG. 2, a boundary line 201 indicating the imaging area, is preferably displayed together with the radiographic image. With the boundary line 201 displayed together with the long image (radiographic image), the operator can recognize that the image has no defect caused by an error.

Figure 3A:
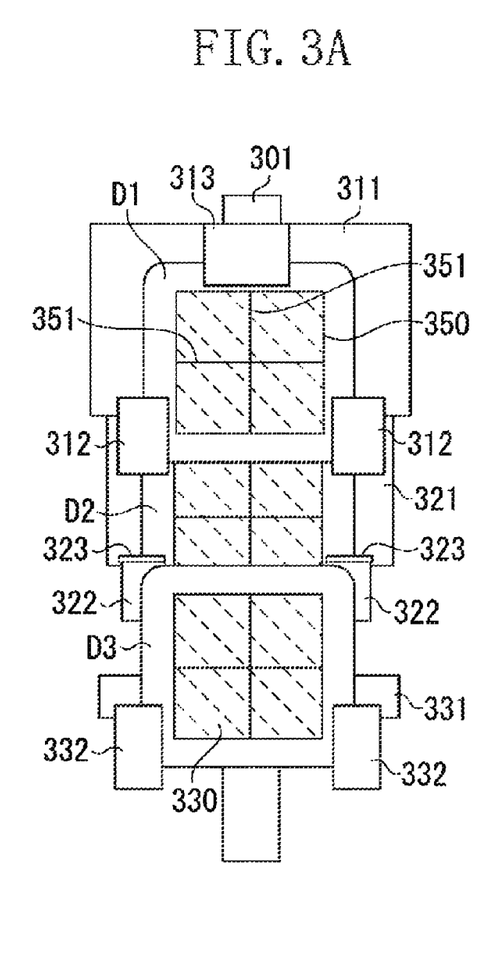
FIGS. 3A and 3B are schematic diagrams illustrating a state of holding radiation imaging apparatuses.
Figure 3B:
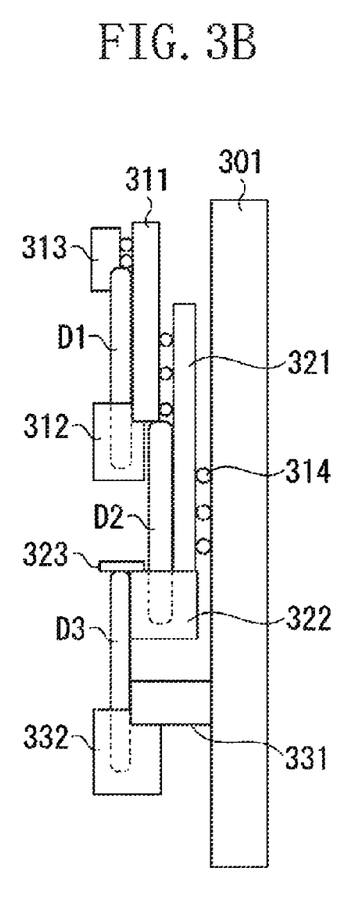
Figure 4A:
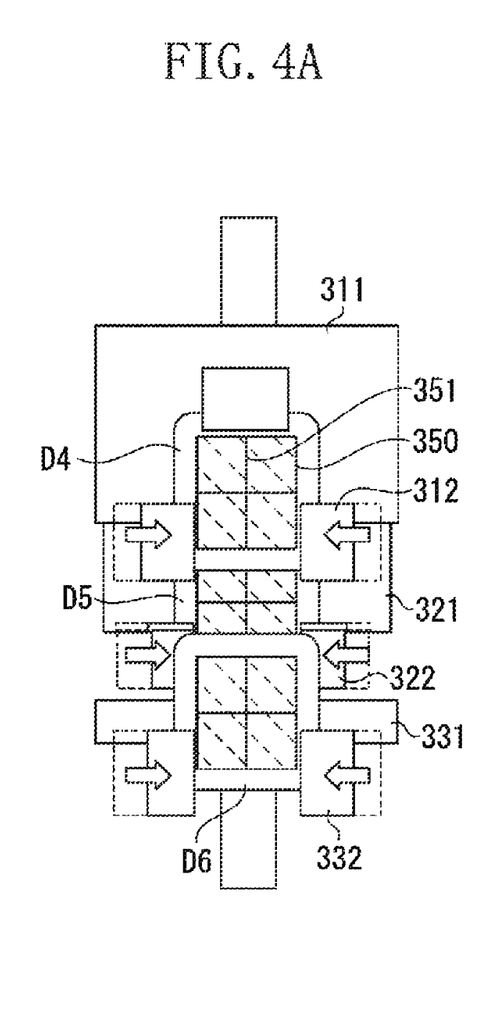
FIGS. 4A and 4B are schematic diagrams illustrating a state of holding radiation imaging apparatuses.
Figure 4B:
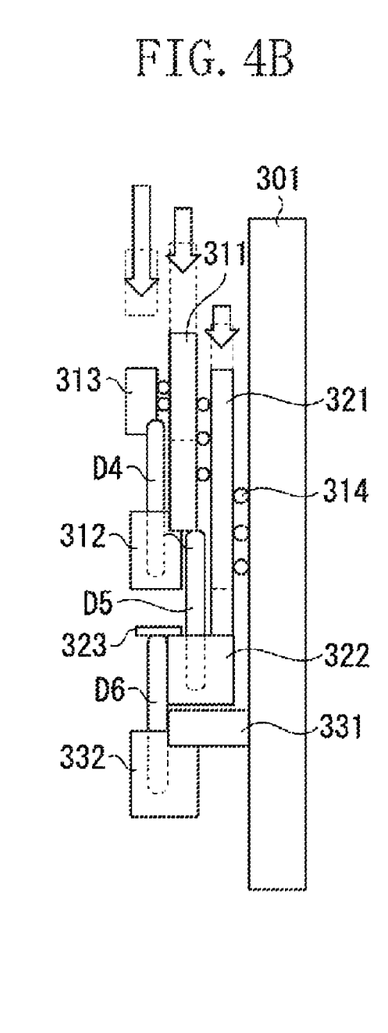

Next, holding states of the radiation imaging apparatuses D1, D2, and D3, accommodated in the radiation imaging system S, are described with reference to FIGS. 3A, 3B, 4A, and 4B. FIGS. 3A and 3B are respectively schematic front and side views illustrating an example of a state where the three radiation imaging apparatuses D1 to D3, having the same size, are held in the radiation imaging system S. FIGS. 4A and 4B are respectively schematic front and side views illustrating an example of a state where three radiation imaging apparatuses D4 to D6 that are smaller than the radiation imaging apparatuses D1 to D3 in the example illustrated in FIGS. 3A and 3B are held in the radiation imaging system S. Each of the radiation imaging apparatuses has an imaging area 330 which includes, on its front surface, an index 350 indicating the imaging area corresponding to the area of the pixel array with which the radiography can be performed, and an aligning index 351 indicating aligning coordinates of the imaging area. A long radiographic image can be obtained, in a combined imaging area 330, by combining images obtained by imaging with the radiation imaging apparatuses overlapped with each other.

A holding unit of this example includes an upper stage connecting member 311, upper stage holding members 312, a middle stage connecting member 321, middle stage holding members 322, a lower stage connecting member 331, and lower stage holding members 332, which are collectively mounted onto a accommodating unit supporting member 301. The radiation imaging apparatuses D1 and D4, in an upper stage of the radiation imaging system S, are positioned and held by the upper stage connecting member 311 and the upper stage holding members 312. The radiation imaging apparatuses D2 and D5, in a middle stage, are positioned and held by the middle stage connecting member 321 and the middle stage holding members 322. The radiation imaging apparatuses D3 and D6, in a lower stage, are positioned and held by the lower stage connecting member 331 and the lower stage holding members 332.

The lower stage connecting member 331 is disposed on a rear side, that is, on a side opposite to the radiation receiving side of the radiation imaging apparatuses D3 and D6, each of which is one of the plurality of radiation imaging apparatuses. The lower stage holding members 332 hold (grip) the radiation imaging apparatuses D3 and D6 at the outside of the imaging area 330 of each of the radiation imaging apparatuses D3 and D6 so that the stage holding members 332 are not included in the radiographic image to be obtained. The lower stage holding members 332 are mechanically connected to the lower stage connecting member 331 so as to be movable, with respect to the lower stage connecting member 331, in a lateral direction intersecting with the longitudinal direction of the long-length imaging. In this manner, the lower stage holding members 332 can move inward as illustrated by the opposing white arrows in FIG. 4A, when the radiation imaging apparatus D6 with a smaller size and imaging area than those of the radiation imaging apparatus D3 is accommodated. Therefore, the radiation imaging apparatus D3 and the radiation imaging apparatus D6 can both be held in a desired position and/or orientation. For example, while the radiation imaging apparatuses D4 and D5 may be held in a landscape orientation, the radiation imaging apparatus D6 may be held in a portrait orientation. The lower stage holding members 332, on both sides in the lateral direction, preferably include a link mechanism (not illustrated) having a centering function for moving the lower stage holding members 332 in an interlocking manner to be equal to each other in a distance to a center position of the radiation imaging system S. In this example, the lower stage connecting member 331 is mechanically connected and thus is fixed to the accommodating unit supporting member 301, and lower stage holding members 332 move (slide) parallel to stage connecting member 331.

The middle stage connecting member 321 is disposed on the rear side of the radiation imaging apparatuses D2 and D5. The middle stage holding members 322 hold (grip) the radiation imaging apparatuses D2 and D5 at the outside of the imaging area of each of the radiation imaging apparatuses D2 and D5. In this way, the middle stage connecting member 321 and the middle stage holding members 322 are prevented from being included in the radiographic image to be obtained. The middle stage holding members 322 are mechanically connected to the middle stage connecting member 321 so as to be movable in the lateral direction with respect to the middle stage connecting member321. Thus, the middle stage holding members 322 move inward as illustrated by the opposing white arrows in FIG. 4A, when the radiation imaging apparatus D5 with a smaller size and imaging area than those of the radiation imaging apparatus D2 is accommodated. In this manner, the radiation imaging apparatus D5 and the radiation imaging apparatus D2 can both be similarly held. The middle stage holding members 322 preferably include a link mechanism (not illustrated) having a centering function for moving the middle stage holding members 322 in an interlocking manner to be equal to each other in a distance to the center position of the radiation imaging system S, as in the case of the lower stage holding members 332. The middle stage connecting member 321 is mechanically connected to the accommodating unit supporting member 301 so as to be movable in the longitudinal direction with respect to at least one of the accommodating unit supporting member 301 and the lower stage connecting member 331. To facilitate movement of the middle stage connecting member 321 in the longitudinal direction, self-lubricating ball bearings 314 are arranged between surfaces of the middle stage connecting member 321 and the accommodating unit supporting member 301. Thus, the middle stage connecting member 321 is movable in the longitudinal direction with respect to a holding member holding the radiation imaging apparatus adjacent to the radiation imaging apparatus held by the middle stage connecting member 321. The middle stage holding members 322 include a movement restriction member (movement limiting member) 323 that moves to a position at which the movement restriction member 323 contacts the radiation imaging apparatus D3 or D6. The movement restriction member 323 thus restricts the movement of the middle stage holding members 322 at the position at which the movement restriction member 323 comes into contact with the radiation imaging apparatus D3 or D6. Thus, the positional relationship between a lower end of the radiation imaging apparatus D2 or D5, held by the middle stage holding members 322, and an upper end of the radiation imaging apparatus D3 or D6 constantly remains the same in the longitudinal direction. Thus, the radiation imaging apparatuses in the middle and the lower stages are positioned to have a predetermined overlapping area, regardless of the size or orientation of the radiation imaging apparatus in the lower stage. Here, an example of the movement restriction member 323 may be a mechanical stop member, such as a metallic protrusion on the accommodating unit supporting member 301.

The upper stage connecting member 311 is disposed on the rear side of the radiation imaging apparatuses D1 and D4. The upper stage holding members 312 hold (grip) the radiation imaging apparatuses D1 and D4 at the outside of the imaging area 330 of each of the radiation imaging apparatuses D1 and D4. Thus, the upper stage connecting member 311 and the upper stage holding members 312 are prevented from being included in the radiographic image to be obtained. The upper stage holding members 312 are mechanically connected to the upper stage connecting member 311 so as to be movable in the lateral direction with respect to the upper stage connecting member 311. Thus, the upper stage holding members 312 move inward as illustrated by the opposing white arrows in FIG. 4A, when the radiation imaging apparatus D4 with a smaller size and imaging area than those of the radiation imaging apparatus D1 is accommodated. In this manner, the radiation imaging apparatus D4 and the radiation imaging apparatus D1 can both be similarly held. Alternatively, the upper stage holding members 312 move laterally in opposite directions to accommodate the radiation imaging apparatus in a landscape orientation and a portrait orientation. The upper stage holding members 312 preferably include a link mechanism (not illustrated) having a centering function for moving the upper stage holding members 312 in an interlocking manner to be equal to each other in a distance to the center position of the radiation imaging system S, as in the cases of the middle stage holding members 322 and the lower stage holding members 332. The upper stage connecting member 311 is mechanically connected to at least one of the accommodating unit supporting member 301 and the middle stage connecting member 321 so as to be movable in the longitudinal direction with respect to at least one of the accommodating unit supporting member 301 and the middle stage connecting member 321. To facilitate longitudinal movement of the upper stage connecting member 311 with respect to at least one of the accommodating unit supporting member 301 and the middle stage connecting member 321, self-lubricating ball bearings 314 are provided therebetween. The movement of the upper stage connecting member 311 is restricted once the upper stage connecting member 311 comes into contact with the radiation imaging apparatus D2 or D5. Thus, the positional relationship between a lower end of the radiation imaging apparatus D1 or D4, held by the upper stage holding members 312, and an upper end of the adjacent radiation imaging apparatus D2 or D5 constantly remains the same in the longitudinal direction. Thus, the radiation imaging apparatuses in the upper and the middle stages are positioned to have a predetermined overlapping area, regardless of the size or orientation of the radiation imaging apparatus in the middle stage. The upper stage connecting member 311 has, on its upper portion, an upper stage restricting member 313 that is movable in the longitudinal direction and holds an upper portion of the radiation imaging apparatus D1 to restrict an upward movement of the radiation imaging apparatus D1.

As illustrated in FIGS. 3A, 3B, 4A, and 4B, the holding unit according to the present exemplary embodiment holds a plurality of radiation imaging apparatuses, having imaging areas of different sizes corresponding to the pixel array, in such a manner that the plurality of radiation imaging apparatuses partially overlap with each other spatially, with predetermined overlapping areas as viewed from the radiation incident side. In addition, the predetermined overlapping areas desirably include sufficient areas for connecting the images with each other while securing large imaging areas as much as possible. Thus, the radiation imaging apparatuses accommodated in the upper, the middle, and the lower stages can be selected to have any desired size or orientation and still have predetermined overlapping areas. As a result, in the radiation imaging system S according to the present exemplary embodiment, the plurality of radiation imaging apparatuses of different sizes can be combined as desired.

Figure 5:
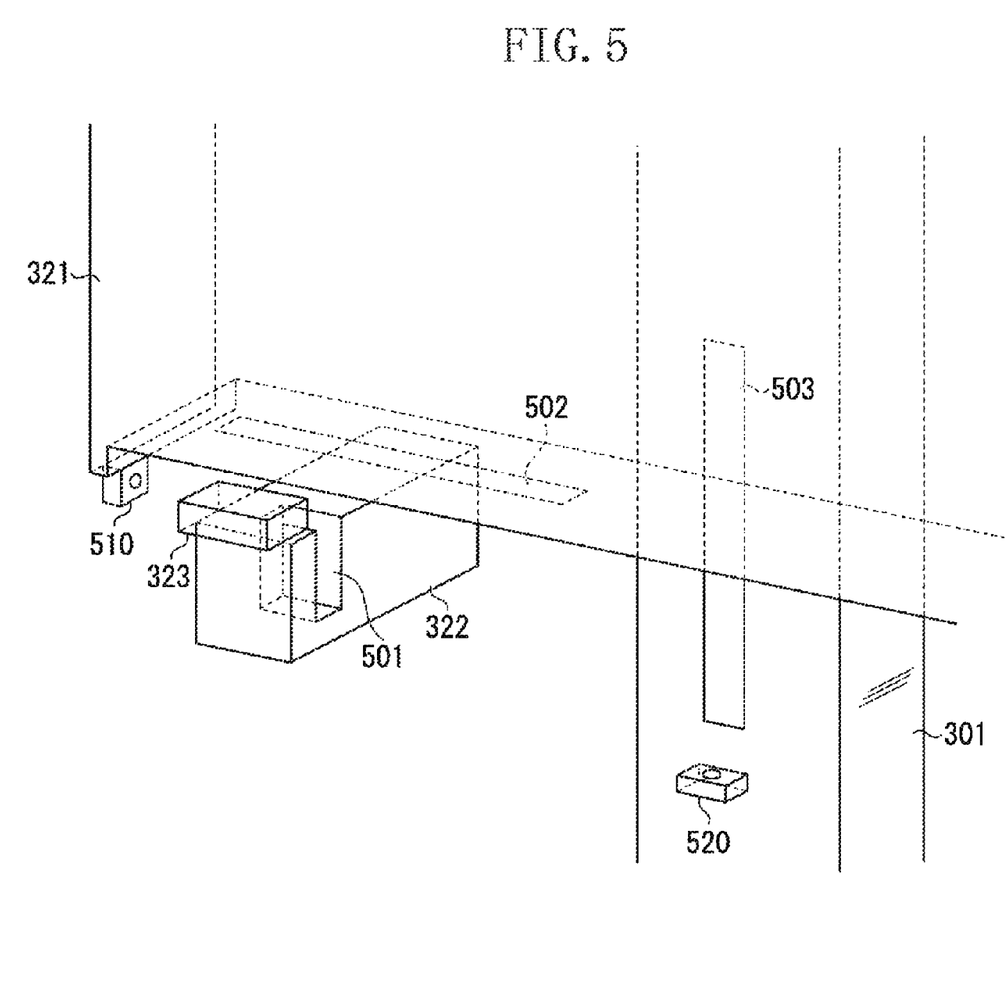
FIG. 5 is a partially enlarged schematic perspective diagram illustrating a configuration of an example of a holding member.

Next, a configuration of the holding member is described in detail with reference to FIG. 5. FIG. 5 is a partially enlarged schematic perspective diagram illustrating the configuration of the holding member in detail, by using the middle stage holding members 322 as an example.

The middle stage holding members 322 each include a receiving area 501 provided with a recess that receives a corner of the radiation imaging apparatus D2. The radiation imaging apparatus D2 inserted from the upper side (in the longitudinal direction) is positioned within an inner wall of the recess of the receiving area 501. The middle stage holding members 322 are each attached to a rail 502, provided to the middle stage connecting member 321, through mechanical connection so as to be movable along the rail 502 in the lateral direction of the long-length imaging area. The middle stage connecting member 321 includes a first measurement unit 510 that is a laser distance meter. The first measurement unit 510 measures position information corresponding to a left and right direction of the holding member 322, that is, the lateral direction of the long-length imaging area along the middle stage connecting member 321, and transmits the position information thus obtained to the radiography control unit 112. The middle stage connecting member 321 is attached to the rail 503, provided to the accommodating unit supporting member 301, through mechanical connection so as to be movable in the upper and lower direction that is the longitudinal direction of the long-length imaging area. The accommodating unit supporting member 301 includes a second measurement unit 520 that is a laser distance meter. The second measurement unit 520 measures position information corresponding to the upper and lower direction of the middle stage connecting member 321, that is, the longitudinal direction of the long-length imaging along the accommodating unit supporting member 301, and transmits the position information thus obtained to the radiography control unit 112.

The configurations of the middle stage holding members 322 and the middle stage connecting member 321 similarly apply to the other holding members and connecting members, and thus the position information corresponding to each stage is similarly transmitted to the radiography control unit 112. The radiography control unit 112 calculates the longitudinal and the lateral dimensions of each of the radiation imaging apparatuses stored in the upper, the middle, and the lower stages based on the corresponding position information, and may use the dimensions for the image processing on the radiographic image, obtained from the radiation imaging system S. The radiography control unit 112 may determine whether an area in which the long-length imaging can be performed by the accommodated radiation imaging apparatuses is large enough for the size of the image to be captured. Based on the determination, the radiography control unit 112 may issue an error notification when the area is insufficient. Alternatively, based on the determination, the radiography control unit 112 may prompt the user to reposition the radiation imaging apparatuses so that an area in which the long-length imaging to be performed by the radiation imaging apparatuses satisfies the size of the image to be captured. Notably, it is contemplated that this feature of using position information of the radiation imaging apparatuses to determine whether the combined imaging area is large enough for the size of the image to be captured can be advantageous in preventing unnecessary radiation to a subject.

Figure 6A:
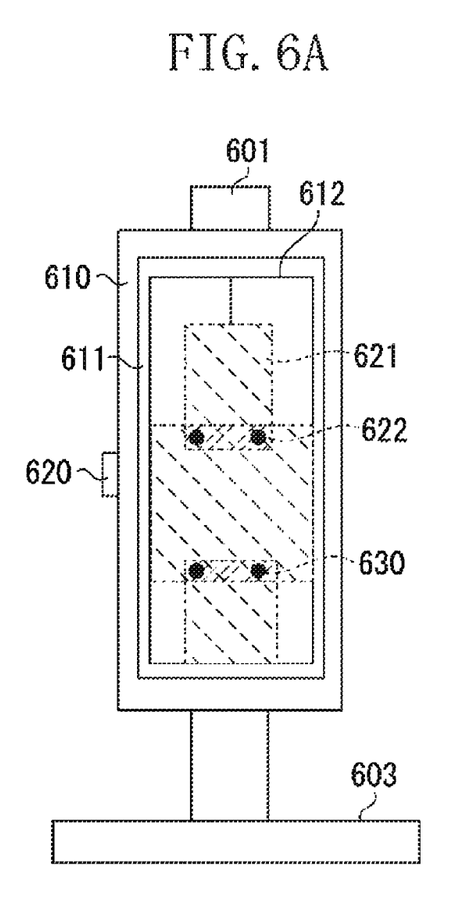
FIGS. 6A and 6B are schematic diagrams illustrating an external structure of the radiation imaging system.
Figure 6B:
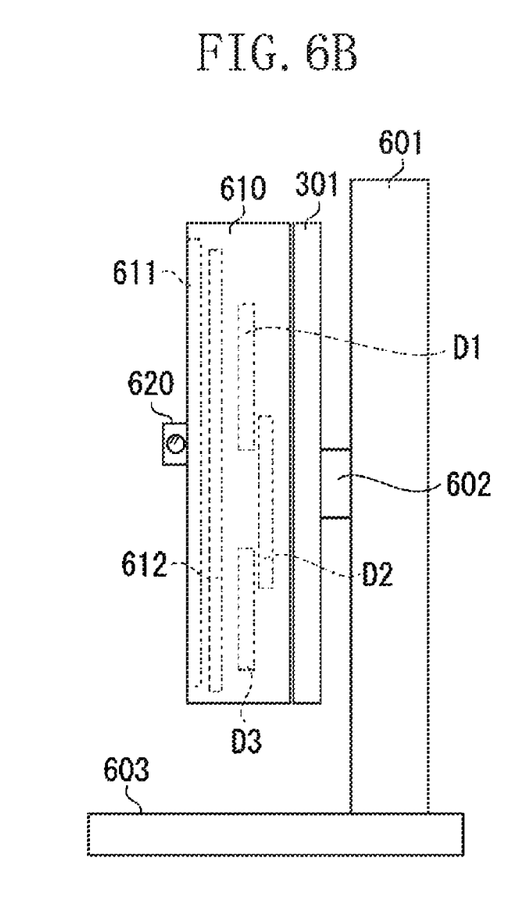

Next, an external configuration of the radiation imaging system S is described with reference to FIGS. 6A and 6B. FIGS. 6A and 6B are schematic diagrams illustrating the external configuration of the radiation imaging system S as viewed from the radiation incident side (front) and a side surface, respectively.

The accommodating member 301 is mechanically connected to a supporting post 601 via a connecting portion 602. The supporting post 601 incorporates a driving unit (not illustrated), such as a motor, capable of moving the connecting portion 602 upward and downward. Thus, the radiation imaging apparatuses D1 to D3 can move in the longitudinal direction in the long-length imaging. The supporting post 601 is fixed to a base 603.

A cover 610 is attached to the accommodating member 301 and covers the radiation imaging apparatuses D1 to D3, the holding units, and the like, to ensure safety. The cover 610 is held by the accommodating member 301 to be openable and closable. Thus, an operation of rearranging, changing orientation, or taking out the radiation imaging apparatuses D1 to D3 can be performed by opening the cover 610. A top plate 611 made of a material with high radiation transmittance, such as an acrylic plate and a carbon fiber reinforced plastic (CFRP) plate and the like, is attached to a surface of the cover 610 on the radiation incident side. The top panel 611 is provided with an index indicating the center position of the imaging area of the long-length imaging. A grid 612 for removing scattered radiation may be attached on an inner side of the top panel 611. An optical projector 620 is provided on a side surface of the cover 610. The optical projector 620 obtains the information on the longitudinal and the lateral dimensions of the long-length imaging to be performed by the radiation imaging apparatuses accommodated in the upper, the middle, and the lower stages from the radiography control unit 112, and optically projects an area 621 in which the long-length imaging can be performed, onto the top panel 611. With the area 621, in which the long-length imaging can be performed, being thus visually recognizable, the imaging portion of the subject can be positioned within the available long-length imaging area. Preferably, the optical projector 620 optically projects overlapping areas 622, between the imaging areas of the radiation imaging apparatuses. It is possible to distinguish the overlapping areas 622 from the area 621 in which the imaging can be performed by differentiating the light illuminance and color from those of the area 621. The operator attaches markers 630 on the top panel 611 on which the overlapping areas 622 are optically projected. Each of the markers 630 can provide a mark (or marker) that is to be included in the radiographic image. Therefore, the markers 630 can include a radiation sensitive member such as a lead ball and the like. Thus, more reliable positioning can be achieved for the radiographic image combining processing, because an image of the same marker 630 is included in both of the images obtained by the radiation imaging apparatuses adjacent to each other. An index indicating a standard area in which the imaging can be performed may be provided on the periphery of the top panel 611. When the imaging is performed without the grid 612, a configuration may be employed that includes the top panel 611 made of a transparent material through which the internal accommodated state of the radiation imaging apparatuses can be checked without any display provided by the optical projector 620.

Figure 7:
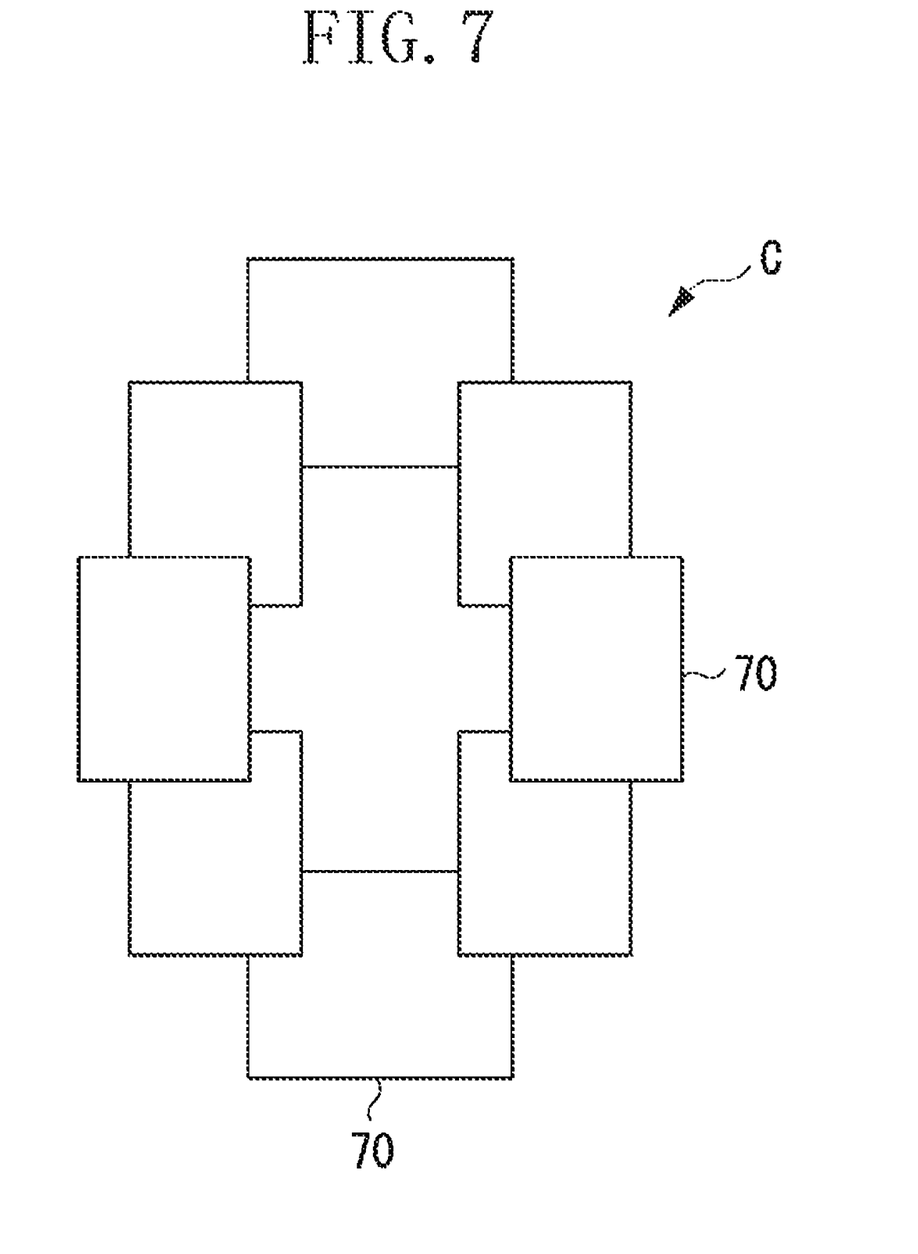
FIG. 7 is a schematic diagram of a collimator suitable for a radiography system according to an exemplary embodiment.

Next, a collimator C suitably used for the radiography system 107 employing the radiation imaging system S according to the present invention is described in detail with reference to FIG. 7. FIG. 7 is a schematic diagram illustrating an arrangement of the collimator C as viewed in a direction from a radiation source 108 to the radiation imaging system S. A general collimator includes four radiation shielding plates to obtain a rectangular irradiation area. With such a collimator, when the radiation emitted area is set for emitting radiation onto all of the radiation imaging apparatuses D with the imaging areas having different lateral dimensions, an area without the radiation imaging apparatuses D (area that does not need to be irradiated with the radiation) is inevitably irradiated with the radiation. Thus, as shown in FIG. 7, the collimator C of this system is configured to include a plurality of radiation shielding plates 70 to form a side of the radiation irradiation area in an arranged direction of the plurality of radiation imaging apparatuses D adjacent to each other. In this configuration, the radiation irradiation area, extending in the arranged direction of the plurality of radiation imaging apparatuses D adjacent to each other, can be moved in a direction intersecting with the arranged direction. In the example illustrated in FIG. 7, the collimator C includes total of eight radiation shielding plates 70, and uses three radiation shielding plates arranged for each side in the arranged direction of the plurality of radiation imaging apparatuses D adjacent to each other, whereby the radiation irradiation area illustrated in FIG. 1B can be formed. Preferably, the radiography control unit 112 performs control so that the positions of the radiation shielding plates 70 of the collimator C are linked with the position information of each of the radiation imaging apparatuses D from the radiation imaging system S, for example. Furthermore, the position of each of the radiation shielding plates 70 may be defined based on an index indicating a position where each of the radiation imaging apparatuses D is disposed based on the size of the radiation imaging apparatus D, provided to the front surface of the radiation imaging system S. Furthermore, efficient long-length imaging can be achieved if the position of each of the radiation imaging apparatuses D and the radiation irradiation area delimited by the collimator C are displayed on the display unit 113 by the radiography control unit 112 in position adjustment before the imaging.

In the examples illustrated in FIGS. 3A, 3B, 4A, and 4B, the radiation imaging apparatuses adjacent to each other are positioned to have predetermined overlapping areas, by fixing and using the position of the lower end of the radiation imaging apparatus accommodated in the lower stage as a reference. However, the present exemplary embodiment is not limited to these examples. In another example, the position of the upper end of the radiation imaging apparatus, accommodated in the upper stage, may be fixed and used as a reference. Another example of the radiation imaging system S is described with reference to FIGS. 8A and 8B, which are respectively front and side views of the other example of the radiation imaging system according to the present invention.

Figure 8A:
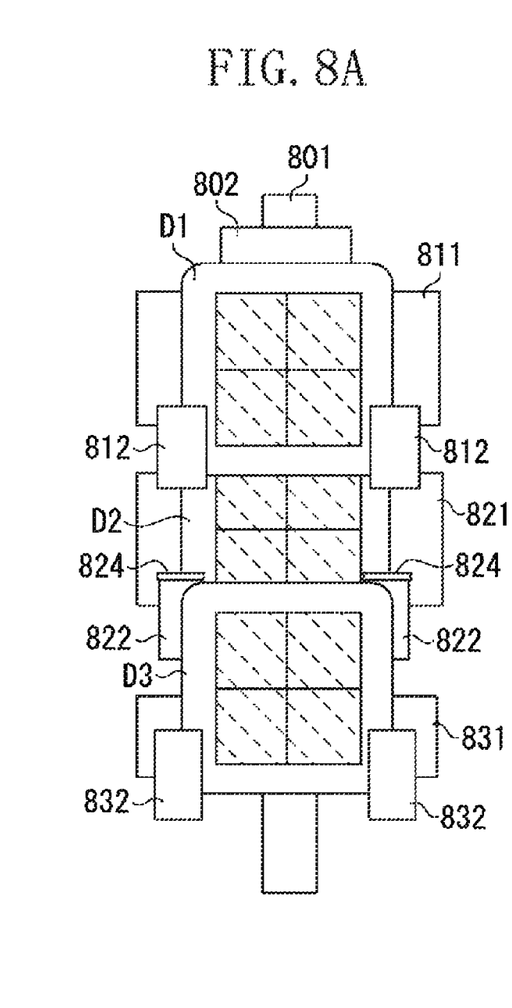
FIGS. 8A and 8B are schematic diagrams illustrating another example of the radiation imaging system according to an exemplary embodiment.
Figure 8B:
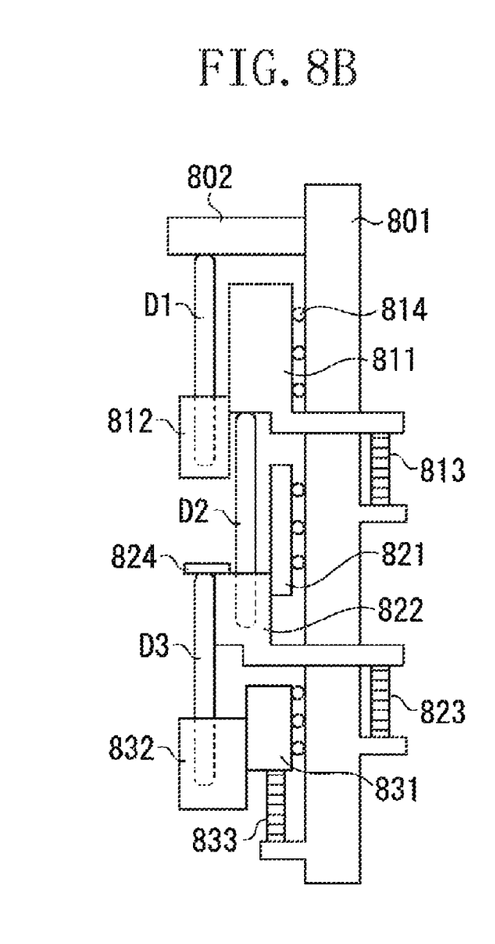

A holding unit according to the other example includes an upper stage connecting member 811, upper stage holding members 812, a middle stage connecting member 821, middle stage holding members 822, a lower stage connecting member 831, lower stage holding members 832, and a position regulating member 802. The radiation imaging apparatus D1, which is one of the plurality of radiation imaging apparatuses disposed in the upper stage of the radiation imaging system S, is held by the upper stage connecting member 811 and the upper stage holding members 812. The radiation imaging apparatus D2, which is disposed in the middle stage of the radiation imaging system S, is held by the middle stage connecting member 821 and the middle stage holding members 822. The radiation imaging apparatus D3, which is disposed in the lower stage of the radiation imaging system S, is held by the lower stage connecting member 831 and the lower stage holding members 832.

The upper stage connecting member 811 is disposed on a rear surface side of the radiation imaging apparatus D1. The upper stage holding members 812 hold or grip the radiation imaging apparatus D1 at the outside of the imaging area of the radiation imaging apparatus D1. Thus, the upper stage connecting member 811 and the upper stage holding members 812 are prevented from being included in the radiographic image to be obtained. The upper stage holding members 812 are mechanically connected to the upper stage connecting member 811 so as to be movable in the lateral direction with respect to the upper stage connecting member 811. The upper stage connecting member 811 is mechanically connected to the accommodating unit supporting member 801 so as to be movable in the longitudinal direction with respect to the accommodating unit supporting member 801 including the movement restriction member 802. The upper stage connecting member 811 is moved by a force exerted by an upper stage elastic member 813, and to facilitate such movement, self-lubricating ball bearings 814 are disposed between opposing surfaces of the accommodating unit supporting member 801 and the upper stage connecting member 811. The upper stage elastic member 813 is disposed between a protrusion of the accommodating unit supporting member 801 and the upper stage connecting member 811 so that the radiation imaging apparatus D1 is moved to a position where the radiation imaging apparatus D1 comes into contact with the movement restriction member 802. A compression spring is suitably used as the elastic member 813, but other mechanically equivalent structures such as a pneumatic shock absorber or telescopic damper may be applicable.

The middle stage connecting member 821 and the lower stage connecting member 831 are mechanically similar to the upper stage connecting member 811. The middle stage connecting member 821 is disposed on the rear side of the radiation imaging apparatus D2. The middle stage holding members 822 hold (grip) the radiation imaging apparatus D2 at the outside of the imaging area of the radiation imaging apparatus D2. Thus, the middle stage connecting member 821 and the middle stage holding members 822 are prevented from being included in the radiographic image obtained. The middle stage holding members 822 are mechanically connected to the middle stage connecting member 821 so as to be movable in the lateral direction with respect to the middle stage connecting member 821. The middle stage connecting member 821 is mechanically connected to the accommodating unit supporting member 801 so as to be movable in the longitudinal direction with respect to the accommodating unit supporting member 801. The middle stage connecting member 821 is moved by an elastic member 823 in the middle stage disposed between a protrusion of the accommodating unit supporting member 801 and the middle stage connecting member 821 so that the radiation imaging apparatus D2 is moved to a position where the radiation imaging apparatus D2 comes into contact with the upper stage connecting member 811. Thus, the positional relationship between the upper end of the radiation imaging apparatus D2 and the upper stage connecting member 811 constantly remains the same in the longitudinal direction of the long-length imaging. Thus, the radiation imaging apparatuses in the upper and the middle stages are positioned to have predetermined overlapping areas, regardless of the size of the radiation imaging apparatus in the middle stage.

The lower stage connecting member 831 is disposed on the rear side of the radiation imaging apparatus D3. The lower stage holding members 832 hold the radiation imaging apparatus D3 at the outside of the imaging area of the radiation imaging apparatus D3. Thus, the lower stage connecting member 831 and the lower stage holding members 832 are prevented from being included in the radiographic image to be obtained. The lower stage holding members 832 are mechanically connected to the lower stage connecting member 831 so as to be movable in the lateral direction with respect to the lower stage connecting member 831. The lower stage connecting member 831 is mechanically connected to the accommodating unit supporting member 801 so as to be movable in the longitudinal direction with respect to the accommodating unit supporting member 801. The middle stage connecting member 821 includes a movement restriction member 824. The lower stage connecting member 831 is moved by an elastic member 833 in the lower stage disposed between a protrusion of the accommodating unit supporting member 801 and the lower stage connecting member 831 so that the radiation imaging apparatus D3 is moved to a position where the radiation imaging apparatus D3 comes into contact with the movement restriction member 824. Thus, the positional relationship between the upper end of the radiation imaging apparatus D3 and the middle stage connecting member 821 constantly remains the same in the longitudinal direction of the long-length imaging. As a result, the radiation imaging apparatuses in the middle and the lower stages are positioned to have predetermined overlapping areas with the respective imaging apparatus respectively above it, regardless of the size of the radiation imaging apparatus in the lower stage.

In this configuration, the radiation imaging apparatuses, selected to have desired sizes, can be disposed in the upper, the middle, and the lower stages while having predetermined overlapping areas. Thus, the radiation imaging apparatuses having a plurality of imaging areas with different sizes can be combined and used more effectively. For example, this configuration is advantageous in a case where the imaging is to be performed on the upper end of the imaging area of the long-length imaging performed by the radiation imaging system S, with the top panel 611 aligned with the chest of the subject while preventing the top panel 611 from being in front of the face of the subject. The reference position may be changeable as desired with the movement restriction member 802 mechanically connected to the accommodating unit supporting member 801 in such a manner as to be movable in the longitudinal direction of the long-length imaging.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-072873, filed Mar. 31, 2015, which is hereby incorporated by reference herein in its entirety.

What is claimed is:

1. A radiation imaging system comprising:
a holding unit configured to hold a plurality of radiation imaging apparatuses configured to convert radiation emitted onto the radiation imaging apparatuses into image signals, and configured to obtain a long-length radiographic image based on the image signals from the plurality of radiation imaging apparatuses,
wherein the holding unit is configured to hold the plurality of radiation imaging apparatuses, having imaging areas of different sizes, in such a manner that each radiation imaging apparatus among the plurality of radiation imaging apparatuses is partially overlapped with each other spatially, by a predetermined overlapping area as viewed from a radiation incident side.

2. The radiation imaging system according to claim 1, wherein the imaging areas are each an area corresponding to a pixel array, including a plurality of pixels arranged in a two-dimensional matrix, included in each of the radiation imaging apparatuses, and
wherein the holding unit is configured to be movable in accordance with the sizes of the image areas.

3. The radiation imaging system according to claim 2, wherein the plurality of radiation imaging apparatuses has sizes corresponding to the sizes of the imaging areas, and
wherein the holding unit is configured to be movable in accordance with the sizes of the plurality of radiation imaging apparatuses.

4. The radiation imaging system according to claim 1, wherein the holding unit includes a holding member configured to hold one of the plurality of radiation imaging apparatuses at an outside portion of a corresponding one of the imaging areas, and a connecting member mechanically connected to the holding member in a state where the holding member is movable, and
wherein the connecting member is disposed on a side of the one of the plurality of radiation imaging apparatuses opposite to the radiation incident side.

5. The radiation imaging system according to claim 4, further comprising:
a supporting member to which the connecting member is mechanically connected,
wherein the connecting member is mechanically connected to the supporting member so as to be movable in a longitudinal direction of the radiographic image, in accordance with the size of the imaging area, and
wherein the holding member is mechanically connected to the connecting member so as to be movable in a lateral direction intersecting with the longitudinal direction.

6. The radiation imaging system according to claim 1, wherein the holding unit includes an upper stage holding member, an upper stage connecting member, a middle stage holding member, a middle stage connecting member, a lower stage holding member, and a lower stage connecting member, wherein the upper stage holding member is configured to hold a radiation imaging apparatus disposed in an upper stage among the plurality of radiation imaging apparatuses, at an outside portion of the imaging area of the radiation imaging apparatus disposed in the upper stage, wherein the upper stage connecting member is mechanically connected to the upper stage holding member in a state of being capable of moving the upper stage holding member, and is disposed on a side of the radiation imaging apparatus disposed in the upper stage opposite to the radiation incident side, wherein the middle stage holding member is configured to hold a radiation imaging apparatus disposed in a middle stage among the plurality of radiation imaging apparatus, at an outside portion of the imaging area of the radiation imaging apparatus disposed in the middle stage, wherein the middle stage connecting member is mechanically connected to the middle stage holding member in a state where the middle stage holding member is movable, and is disposed on a side of the radiation imaging apparatus disposed in the middle stage opposite to the radiation incident side, wherein the lower stage holding member is configured to hold a radiation imaging apparatus disposed in a lower stage among the plurality of radiation imaging apparatus, at an outside portion of the imaging area of the radiation imaging apparatus disposed in the lower stage, and wherein the lower stage connecting member is mechanically connected to the lower stage holding member in a state where the lower stage holding member is movable, and is disposed on a side of the radiation imaging apparatus disposed in the lower stage opposite to the radiation incident side.

7. The radiation imaging system according to claim 6, further comprising:

a supporting member to which the upper stage connecting member, the middle stage connecting member, and the lower stage connecting member are mechanically connected, wherein the lower stage connecting member is fixed to the supporting member, and a movement of the middle stage connecting member is restricted at a position where a movement restriction member, provided to the middle stage holding member, comes into contact with the radiation imaging apparatus disposed in the lower stage.

8. The radiation imaging system according to claim 7, wherein a movement of the upper stage connecting member is restricted at a position where the upper stage connecting member comes into contact with the radiation imaging apparatus disposed in the middle stage.

9. The radiation imaging system according to claim 6, further comprising:

a supporting member to which the upper stage connecting member, the middle stage connecting member, and the lower stage connecting member are mechanically connected, wherein the upper stage connecting member moves to a position where the radiation imaging apparatus in the upper stage comes into contact with a movement restriction member of the supporting member by an upper stage elastic member disposed between the upper stage connecting member and a protrusion of the supporting member, and wherein the middle stage connecting member moves to a position where the radiation imaging apparatus in the middle stage comes into contact with the upper stage connecting member by an middle stage elastic member disposed between the middle stage connecting member and a protrusion of the supporting member.

10. The radiation imaging system according to claim 9, wherein the lower stage connecting member moves to a position where the radiation imaging apparatus in the lower stage comes into contact with a movement restriction member of the middle stage connecting member by an lower stage elastic member disposed between the lower stage connecting member and a protrusion of the supporting member.

11. The radiation imaging system according to claim 6, wherein the upper stage holding member is mechanically connected to the upper stage connecting member so as to be movable in a lateral direction intersecting with a longitudinal direction of the radiographic image, wherein the middle stage holding member is mechanically connected to the middle stage connecting member so as to be movable in the lateral direction, and wherein the lower stage holding member is mechanically connected to the lower stage connecting member so as to be movable in the lateral direction.

12. The radiation imaging system according to claim 4, further comprising:

a first measurement unit configured to measure position information corresponding to a lateral direction, intersecting with a longitudinal direction of the radiographic image, of the holding unit;

a second measurement unit configured to measure position information corresponding to the longitudinal direction of the connecting member; and a control unit configured to perform overall control on image processing executed by the radiation imaging system, wherein the control unit is configured to determine whether an area in which long-length imaging is possible by the plurality of radiation imaging apparatuses is sufficient for a size of the imaging, based on the position information transmitted from the first measurement unit and the position information transmitted from the second measurement unit.

13. The radiation imaging system according to claim 12, further comprising:

an accommodating member and a cover configured to accommodate the plurality of radiation imaging apparatuses and the holding unit; and wherein a top panel is attached to a surface of the cover on the radiation emitting side, wherein an optical projector is provided on a side surface of the cover, and wherein the optical projector is configured to optically project an area in which long-length imaging is possible onto the top panel, based on information from the control unit.

14. A radiography system comprising:

the radiation imaging system according to claim 1;

a radiation source configured to emit radiation onto an object; and a collimator disposed between the radiation source and the radiation imaging system, and configured to delimit an irradiation area irradiated with the radiation, wherein the collimator is configured to shift the irradiation area, extending in an arranged direction of the plurality of radiation imaging apparatuses, in a direction intersecting with the arranged direction.

15. A radiation imaging system comprising:
a holding unit configured to hold a plurality of radiation imaging apparatuses configured to convert radiation emitted onto the radiation imaging apparatuses into image signals, and configured to obtain a long radiographic image based on the image signals from the plurality of radiation imaging apparatuses, and
wherein the holding unit is configured to hold the plurality of radiation imaging apparatuses in such a manner that the plurality of radiation imaging apparatuses is partially overlapped with each other spatially, by a predetermined overlapping area as viewed from a radiation incident side, by holding only one of the radiation imaging apparatuses that has a first imaging area or only one of the radiation imaging apparatuses that has a second imaging area different from the first imaging area.

16. The radiation imaging system according to claim 15, wherein the holding unit is configured to be movable in accordance with a size of a corresponding one of the first imaging area and the second imaging area.

17. The radiation imaging system according to claim 15, wherein the second imaging area has a larger area than the first imaging area, as viewed from the radiation incident side.

* * * * *